United States Patent [19]

Kresjun et al.

[11] Patent Number: 4,908,374
[45] Date of Patent: Mar. 13, 1990

[54] PHARMACEUTICAL PREPARATION FOR PROPHYLAXIS AND TREATMENT OF ALCOHOLISM

[76] Inventors: Valentin I. Kresjun, ulitsa 25-oi, Chapaevskoi divizii 5, kv. 69; Vadim L. Aryaev, ulitsa Perekopskoi, divizii 17, kv. 14, both of Odessa; Georgy M. Rudenko, ulitsa Sadovo-Kudrinskaya 23, kv. 32; Andrei G. Vrublevsky, ulitsa Akademika Millionsohikova 16, kv. 206, both of Moscow; Fedor I. Kostev, ulitsa Akademika Vilyamsa 54, korpus 2, kv. 197; Roman Y. Maximovich,deceased; Roman Y. Maximovich Jr, administrator, both of ulitsa Perekopskoi divizii 16a, kv. 28, Odessa, all of U.S.S.R.

[21] Appl. No.: 281,247
[22] Filed: Dec. 7, 1988
[51] Int. Cl.⁴ .......................................... A61K 31/445
[52] U.S. Cl. .................................................... 514/330
[58] Field of Search ......................................... 514/330

[56] References Cited
PUBLICATIONS

Chem. Abst. 99-171147B (1983).
Chem. Abst. 100-203485T (1984).

*Primary Examiner*—Stanley J. Friedman
*Attorney, Agent, or Firm*—Burgess, Ryan & Wayne

[57] ABSTRACT

A pharmaceutical preparation for prophylaxis and treatment of alcoholism comprises an active principle which is nicotinic acid lithium salt semihydrate of the formula:

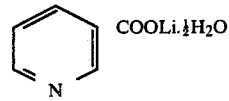

and a pharmaceutically acceptable vehicle.

8 Claims, No Drawings

PHARMACEUTICAL PREPARATION FOR PROPHYLAXIS AND TREATMENT OF ALCOHOLISM

FIELD OF THE INVENTION

The present invention relates to medicine and, more particularly, to a pharmaceutical preparation intended for the treatment and prophylaxis of alcoholism which is useful in psychyatry for therapy of chronic alcoholism and cutting-short of the alcoholic abstinent syndrome. It is also possible to use the preparation in healthy persons under stress conditions, since it possesses also stress-protective and tranquilizing properties.

Prior Art

Known in the art are various preparations possessing antialcoholic properties. They can be exemplified by preparations of sensitizing, aversive and psychotropic effects. Among them most widely employed are psychotropic preparations which differ advantageously from sensitizing and aversive preparations both in stability and duration of therapeutic remissions and in resocialization of patients suffering from alcoholism (Zdravookhranenie Tadzhikistana, No. 1, Jan. 1981/Dushanbe/, Kamolov Sh.K., Comparative Effectiveness of Antialcoholic Methods of Treatment, pp. 69–71). In this group of pharmaceutical preparations the highest activity is exhibited by neuroleptcis or tranquilizers especially based on derivatives of phenothiazine and benzodiazepine. However, in therapy of alcoholism neuroleptics produce pronounced side effects such as locomotive retardation, constraints, muscle twitching, parkinsonism phenomena and the like. Administration of benzodiazepine derivatives to such patients is also accompanied by a whole number of complications: development of toleration, formation of medicinal dependence. Since therapy of chronic alcoholism envisages a lasting administration of pharmaceutical preparations, the above-described phenomena are encountered far more frequently in the treatment of alcoholism than in the case of other psychopathological disturbances. The above-mentioned complications hinder a broad application of said prior art preparations as antialcoholic agents.

The data available from the literature point out that in pharmacotherapy of alcoholism especially active are pharmaceutical preparations based on lithium salts. Effectiveness of such preparations in the treatment of alcoholism is caused by the specific feature of lithium salts, residing in their ability of actively influence pathogenetic units of the process of development of alcoholism and accompanying affective disturbances, disorders of the emotional status.

Most widely used in the clinical practice are pharmaceutical preparations based on lithium chloride or lithium carbonate. Therapeutic activity of these preparations is revealed only under the conditions of their administration in high doses for creation of a high concentration of lithium in blood (1.5-−2 mequiv/1) which necessitates a permanent laboratory control. Their administration in the above-specified doses is accompanied by side and toxic phenomena, especially pronounced on the part of kidneys. Furthermore, the preparation based on lithium carbonate has no soluble pharmaceutically acceptable form, while that based on lithium chloride has clearly pronounced hydroscopic properties. All this hampers a wide application of these preparations for the treatment of alcoholism.

SUMMARY OF THE INVENTION

It is an object of the present invention to provide a pharmaceutical preparation for prophylaxis and therapy of alcoholism, possessing a high effectiveness with absence of side and toxic effects in a suitable pharmaceutical form.

The object of the present invention is to provide a pharmaceutical preparation based on an active principle which, according to the present invention, is nicotinic acid lithium salt semihydrate of the general formula:

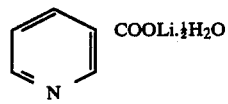

in combination with a pharmaceutical acceptable vehicle.

It is advisable that the pharmaceutical preparation according to the present invention be used in the form of a solution for injections containing 10% by mass of the active principle in combination with a pharmaceutically acceptable vehicle such as distilled water or an isotonic solution. Such preparation accelerates arresting of the alcoholic abstinent syndrome, improves the accuracy of dosage and provides an opportunity of administration thereof in the case of a forced therapy of alcoholism.

For an ambulatory treatment and prevention of hard-drinking periods it is advisable to administer the pharmaceutical preparation according to the present invention in the form of pills containing 40% by mass of the active principle in combination with a pharmaceutically acceptable vehicle.

As the pharmaceutically acceptable vehicle use can be made of stearic acid, lactose, glucose, potato starch, talc.

DETAILED DESCRIPTION OF THE INVENTION

To obtain nicotnic acid lithium salt semihydrate(lithium nicotinate semihydrate), lithium carbonate is mixed with nicotinic acid in equimolar amounts in 200 ml of distilled water. The reaction mixture is heated to the temperature of 90° C., and maintained at this temperature till complete dissolution of the reactants and stopping of evolution of carbon dioxide gas. The resulting solution is treated with 2 g of activated carbon in the presence of ethanol, cooled to a temperature of 10°–12° C., whereafter the resulting crystals of lithium nicotinate semihydrate are filtered-off and dried at a temperature of 105°–110° C. The total yield of the desired high-purity product is 80–98%. The resulting substance has not been hitherto described in the literature. The compound comprises a white crystalline powder having no odor, with a slight bitter taste. Stable in air. Readily soluble in water, sparingly soluble in absolutized ethanol. The pH of a 5% aqueous solution of the compound is 7.8–9.0 (potentiometrically). The 5% solution is colorless and transparent. With increasing concentration of the solution till saturation (45%) a yellow color appears, the solution acquires a viscous consistence, its specific gravity and refractive index are increased:

for a 1% solution $\rho_4^{20} = 1.0077; \eta_D^{20} = 1.3370$ for a 44% solution $\rho_4^{20} = 1.2428; \eta_D^{20} = 1.4460$ The electrical conductivity of diluted solutions of lithium nicotinate semihydrate is increased. The dissociation constant calculated from the data of molecular electrical conductivity measurements is equal to $5.6 \times 10^3$.

The character of variations of these values made it possible to assume that in concentrated solutions and in solid state the resulting substance exists in the form of associates.

Thermogravimetric studies have shown that the compound is thermally stable at a temperature within the range of from 0° to 180° C. Dehydration occurs at a temperature of from 180° to 220° C.; clear-cut melting is absent; decomposition of the compound occurs at a temperature within the range of from 400° to 550° C.

The product is identified for nicotinic acid and lithium by gravimetric, iodometric and spectrophotometric methods.

Found, %: C 49.22, H 4.05, N 9.68, O 32.43, Li 4.62, nicotinic acid 89.0, lithium 4.7.

Calculated, %: C 49.10, H 4.11, N 9.58, O 32.47, Li 4.75, nicotinic acid 88.8, lithium 4.71.

Recording of spectra by the IR-spectroscopy method was effected under standardized conditions using a two-beam spectrophotometer IKS-14 with prisms within the range of from 4.000 to 650 cm$^{-1}$. Samples were pressed in tablets of potassium bromide. The test salt-lithium nicotinate semihydrate had the following characteristic lines: 3,370–3,228 cm$^{-1}$; 14,020–1.400 cm$^{-1}$; 1,310–1,290 cm$^{-1}$; 850, 830 and 748 cm$^{-1}$.

The pharmaceutical preparation for prevention and treatment of alcoholism was obtained on the basis of lithium nicotinate semihydrate with the above-given characteristics.

To obtain an injection pharmaceutical form, a 10% solution of the active principle in distilled water or in an isotonic solution is prepared.

To obtain a pelletized pharmaceutical form (dragee) conventional techniques are employed (100 mg of the active principle per 250 mg of the total mass of dragee pellets) (i.e., 40% by mass).

The pharmaceutical preparation according to the present invention is stable. Its shelf life is 3 years. Storage conditions: in a dry, light-protected place.

The study of the specific activity of the preparation was performed in detail experimentally on white rats and on patients in clinics.

In experiments the animals were administered with intraperitoneal injections of the preparation in the dose of 10 mg/kg of the bodymass. This dosage has been established as a result of preliminary experiments. It has been shown that upon administration of the preparation in the dose of 1-3-5-7-9 mg/kg of the bodymass the therapeutic effect is not clearly pronounced. Upon administration of the preparation in a dose of from 15 to 25 mg/kg its efficiency is slightly diminished. The dose of 10 mg/kg turned to be optimal.

For the sake of convenience, nicotinic acid lithium salt semihydrate will be referred to hereinafter as lithium nicotinate.

The preparation according to the present invention in in vivo experiments on white nondescript rats reveals a high activity in therapy of analogs of psychological (I), physical (II) stages of the alcoholic dependence, as well as in its preventive use in the course of the formation of addition to ethanol and arresting of the alcoholic abstinent syndrome which opens a new perspective in prophylaxis and treatment of alcoholism.

Screening studies of lithium nicotinate were carried out following standard procedures developed in the Laboratory for finding and investigation of agents for therapy and prevention of narcomania at the Institute of Pharmacology of the USSR Academy of Medical Sciences (Burov Yu.V., Kampov-PoleVoy A.B., Zhukov V.N., Methodical Guidelines on Experimental/Pharmacological/Study of Preparations Suggested for Clinical Testing as Agents for Treatment and Prophylaxis of Alcoholism, Moscow, USSR Ministry of Health Publishing House, 1980, p. 21). Comparison of antialcoholic properties of lithium nicotinate was effected mainly with lithium chloride and lithium carbonate as most widely used and well studied lithium salts. However, as regards key parameters such as antiabstinent activity, the data on lithium nicotinate were compared with another novel pharmaceutical compound possessing a clearly pronounced antiabstinent activity—with lithium hydroxybutyrate.

The assessment of antialcoholic properties of lithium nicotinate was started for evaluation of its efficacy in the course of the formation of alcoholic dependence.

To this end, 160 white rats were placed for 31 days into individual cages with access to a 15% solution of ethanol in water. Every day, once a day, the quantity of ethanol consumed by the animals was measured. The data obtained during the first 10 days were used as the background. On completion of the background alcoholization the rats employed for the experiment were divided into 4 groups: control one and 3 test groups. These groups were composed of an equal number of both "drinking" and "non-drinking" rats of approximately 40 animals in each group. The animals which since the first days of alcoholization volunatrily preferred the solution of ethanol rather than water and consumed it in a quantity of not less than 2 ml/kg of the bodymass were regarded as belonging to the category of "drinking" rats. The rats that preferred water or consumed ethanol in supersmall doses were considered as "non-drinking" category of the animals. Lithium nicotinate, lithium chloride or lithium carbonate were administered to the animals of the test groups against the continued alcoholization in the doses of 10 mg/kg for the period of 14 days. The control rats were administered with injections of distilled water in the same doses and within the same time limits. The percentage of "drinking" rats and the quantity of alcohol consumed by them were calculated. The number of animals consuming daily not less than 2 ml/kg of ethanol during the background period was assumed as 100% and on the basis of this parameter the percentage of rats preferring alcohol during later periods was calculated. The statistic processing of the obtained data was effected by conventional methods. The effectiveness of administration of the pharmaceutical preparation was assessed by two main indicators—an increase in the percentage of "non-drinking" rats in each group in relation to the background and by a decrease in the quantity of alcohol consumed by each animal.

It has been found that lithium nicotinate inhibits the formation of addiction to alcohol. The course administration of the pharmaceutical composition according to the present invention has considerably lowered the alcoholic motivation which was revealed in a certain diminution of percentage of the "drinking" animals and reduction of the volume of alcohol consumed by them (see Tables 1 and 2).

to a 15% solution of ethanol and water. As it is known, during these very periods stable analogs are formed in

TABLE 1

| Nos | Time of investigation | Statistical indicators | | Number of animals (in percent preferring ethanol to water) | | | |
|---|---|---|---|---|---|---|---|
| | Background | M | | 100.0 | 100.0 | 100.0 | 100.0 |
| 1 | 2 | 3 | | 4 | 5 | 6 | 7 |
| | | | | | Administered substances | | |
| | | | | Lithium nicotinate | Lithium chloride | Lithium carbonate | Distilled water |
| 2 | 1-st week of administration of the pharmaceutical preparation | M ± m P | | 50.0 13.4 <0.05 | 71.0 12.1 >0.05 | 71.0 12.1 <0.05 | 86.0 9.3 <0.05 |
| 3 | 2 weeks of administration of the pharmaceutical preparation | M ± m P | | 29.0 12.1 <0.001 | 50.0 13.4 <0.05 | 64.0 12.8 >0.1 | 93.0 6.8 <0.05 |
| 4 | 1 week after cancellation | M ± m P | | 29.0 12.1 <0.001 | 50.0 13.4 <0.05 | 71.0 12.1 >0.05 | 93.0 6.8 <0.05 |

TABLE 2

| Nos | Time of investigation | Statistical indexes* | | Average daily consumption of ethanol in ml per 1 kg of bodymass | | | |
|---|---|---|---|---|---|---|---|
| | Background | M | | 18.1 | 17.6 | 19.3 | 17.1 |
| 1 | 2 | 3 | | 4 | 5 | 6 | 7 |
| | | | | | Administered substances | | |
| | | | | Lithium nicotinate | Lithium chloride | Lithium carbonate | Distilled water |
| 2 | 1-st week of administration of the pharmaceutical preparation | M P | | 15.1 <0.001 | 15.7 <0.05 | 16.1 <0.01 | 17.1 >0.05 |
| 3 | 2 weeks of administration of the pharmaceutical preparation | M P | | 12.5 <0.01 | 15.6 <0.05 | 15.5 <0.05 | 18.5 >0.05 |
| 4 | One week after cancellation | M P | | 13.8 <0.05 | 16.2 >0.05 | 18.5 >0.05 | 18.5 >0.05 |

*Note:
Statistical processing of the data has been performed by the Meddis method.

While in the control group 93.0±6.8% of the animals preferred ethanol to water, after a course administration of lithium nicotinate the number of "drinking rats was only 29.0±12.1% /p<0.01/. Consumption of alcohol by each animal in this case was reduced by 30.9% /p<0.05/. Lithium chloride administered under similar conditions reduced percentage of rats-"alcoholics" from 93.0±6.8% to 50.0±13.4% /p<0.01/ with reduction of the volume of the consumed ethanol by only 11.4% /p<0.05/. In the case of administration of lithium carbonate the number of animals that preferred ethanol remained unchanged. However, the daily average consumption of alcohol was reduced by /19.7% /p<0.01/.

The data given hereinabove demonstrate that lithium nicotinate has the ability of inhibiting formation of addiction to ethanol. The effect of this compound is substantially superior to the therapeutic activity of known salts—lithium chloride and lithium carbonate.

Having obtained the data on the effect of lithium nicotinate on the process of formation of addiction to alcohol we have studied the effectiveness of the preparation according to the present invention in the state of an induced alcoholic dependence and abstinent syndrome.

The study of therapeutic activity of lithium nicotinate in the treatment of an induced alcoholic dependence was carried out on 2 series of white rats stably consuming relatively great (50–60 ml/kg) and relatively small (20–30 ml/kg) of ethanol with 40 animals in each series (20 control and 20 test rats). The animals of both groups with a pronounced alcoholic motivation were selected according to the results of a preliminary 10-days' testing. Alcoholization of the chosen animals was carried out for 3 and 8 months under conditions of a free access rats regarding the "psychological" and "physical" alcoholic dependence. The daily consumption of ethanol over a week prior to administration of lithium nicotinate and during two weeks of its application in the dose of 10 mg/kg was compared. Similar experiments were carried out in the case of administration of lithium chloride and lithium carbonate. The obtained data were also subjected to a statistical processing.

It has been found that lithium nicotinate causes a considerable lowering of ethanol consumption in both test groups during all periods of alcoholization. In 3-months' rats "alcoholics" in the group of "low-drinking" animals the reduction of ethanol consumption under the influence of the preparation was by more than 2 times (10.4 ml/kg relative to 25.9 ml/kg before treatment, p<0.01) as it is seen from Table 3 hereinbelow.

TABLE 3

| Administered compound | Statistical parameters | Daily average consumption of ethanol in ml per kg of the bodymass | | | |
|---|---|---|---|---|---|
| | | Background | 1 week of injections | 2 weeks of injections | One week after cancellation |
| Lithium nicotinate | M P | 25.9 — | 21.7 <0.05 | 10.4 <0.01 | 11.5 <0.01 |
| Lithium chloride | M P | 25.3 — | 22.2 <0.05 | 19.9 <0.05 | 21.6 <0.05 |
| Lithium carbonate | M P | 25.2 — | 22.8 <0.05 | 20.3 <0.01 | 20.6 <0.05 |
| Control | M P | 26.4 — | 25.1 >0.05 | 26.0 >0.05 | 25.1 >0.05 |

Similar results were obtained in the group of "low-drinking" animals, as it is seen from Table 4 hereinbelow.

TABLE 4

| Administered compounds | Statistical parameters | Average daily consumption of ethanol in ml per kg of bodymass | | | |
|---|---|---|---|---|---|
| | | Background | 1 week of injections | 2 weeks of injections | 1 week after cancellation |
| Lithium nicotinate | M | 55.8 | 49.6 | 34.3 | 41.8 |
| | P | — | <0.05 | <0.01 | <0.01 |
| Lithium chloride | M | 46.3 | 41.8 | 37.2 | 39.9 |
| | P | — | <0.01 | <0.01 | <0.01 |
| Lithium carbonate | M | 53.9 | 53.3 | 48.4 | 50.8 |
| | P | — | >0.05 | <0.05 | <0.05 |
| Control | M | 51.6 | 56.3 | 56.2 | 56.6 |
| | P | — | >0.05 | >0.05 | >0.05 |

Against the background of 8 months of alcoholization in the group of "low-drinking" rats lithium nicotinate, as shown in Table 5, reduced the amount of alcohol consumed over the day nearly by half. Lithium chloride administered under the same conditions and in the same doses reduce the consumption of ethanol by 19.7 and 17.4% respectively, lithium carbonate - by 19.4 and 13.4%. Equally convincing regularity was noted in the case of "hard-drinking" white rats, as it is shown in Table 6 hereinbelow.

TABLE 5

| Administered compounds | Statistical parameters | Average daily consumption of ethanol in ml per kg of bodymass | | | |
|---|---|---|---|---|---|
| | | Background | 1st week of injections | 2 weeks of injections | 1 week after cancellation |
| Lithium nicotinate | M | 27.2 | 22.6 | 14.5 | 15.7 |
| | P | | <0.01 | <0.01 | <0.01 |
| Lithium chloride | M | 28.8 | 24.7 | 23.8 | 25.6 |
| | P | | <0.05 | <0.05 | <0.05 |
| Lithium carbonate | M | 22.4 | 19.8 | 19.4 | 19.6 |
| | P | | <0.05 | <0.05 | <0.05 |
| Control | M | 27.8 | 27.9 | 28.8 | 27.7 |
| | P | — | >0.05 | >0.05 | >0.05 |

TABLE 6

| Administered compounds | Statistical parameters | Average daily consumption of ethanol in ml per kg of bodymass | | | |
|---|---|---|---|---|---|
| | | Background | 1st week of injections | 2 week of injections | 1 week after cancellation |
| Lithium nicotinate | M | 67.0 | 54.4 | 42.6 | 50.4 |
| | P | | <0.01 | <0.01 | <0.01 |
| Lithium chloride | M | 62.2 | 68.7 | 63.4 | 56.0 |
| | P | | <0.01 | <0.01 | <0.05 |
| Lithium carbonate | M | 63.2 | 61.1 | 57.9 | 58.3 |
| | P | | >0.05 | <0.05 | <0.05 |
| Control | M | 63.2 | 62.9 | 65.1 | 63.3 |
| | P | — | >0.05 | >0.05 | >0.05 |

Therefore, in experiments on white rats it has been found that under conditions of a formed alcoholic dependence lithium nicotinate exhibits pronounced antialcoholic properties. As regards the degree of deprivation, lithium nicotinate shows a higher activity than lithium chloride or lithium carbonate which corresponds to the results of experiments on investigations into the effect of lithium preparations on the formation of alcoholism.

The study of antiabstinent properties of lithium nicotinate was carried out on 50 white rats, 10 one-month "alcoholics" deprived of the access to ethanol for a week. The obtained data were compared with the results of the study of antiabstinent effects of lithium chloride and lithium carbonate and, what is most important, with lithium hydroxybutyrate having activity considerably surpassing, in this respect, those of standard lithium salts such as lithium chloride and lithium carbonate.

The pronouncedness of the antiabstinent activity in experiment is demonstrated by the effect of pharmaceutical compositions on the level of pathological alcoholic motivation. The level of motivation was assessed by a reduced consumption of alcohol by treated white rats—10-months "alcoholics" having free access to ethanol on completion of a week's period of its deprivation.

It has been found that the period of abstinence in rats of the control group anxiety was noted along with increased locomotive activity, tremor of limbs, refusal from taking meals. Deprivation of ethanol also resulted in an increased demand for it and upon a secondary access to a solution of ethanol the control animals consumed it by 20.9% more than prior to deprivation (87.2 ml/kg vs. 72.1 ml/kg before deprivation, $p<0.01$). In rats treated with lithium nicotinate the above-described phenomena were revealed far weaker. The animals showed no signs of anxiety, tremor of limbs was absent, no refusal from taking meals or water was observed. On completion of the course of the antialcoholic therapy upon a secondary access to ethanol the animals consumed alcohol by 23.8% less than prior to the treatment (56.9 ml/kg vs. 74.4 ml/kg, $p<0.05$). Lithium carbonate and lithium chloride produced a considerably weaker effect on signs of the abstinent syndrome as it is seen from Table 7 hereinbelow.

TABLE 7

| Administered compounds | Statistical parameter | Daily average consumption of ethanol in ml per kg of bodymass | |
|---|---|---|---|
| | | Background | One week of administration of the preparation after a 7-days' deprivation of access there to |
| Lithium nicotinate | M | 74.7 | 56.9 |
| | P | — | <0.01 |
| Lithium chloride | M | 77.5 | 64.8 |
| | P | — | <0.05 |
| Lithium carbonate | M | 70.1 | 59.7 |
| | P | — | <0.05 |
| Lithium hydroxybutyrate | M | 76.2 | 58.5 |
| | P | — | <0.01 |
| Control | M | 72.1 | 87.2 |
| | P | — | <0.01 |

The effect produced by lithium hydroxybutyrate proved to be more intensive than that of lithium chloride and lithium carbonate, but still it was weaker than the effect of lithium nicotinate. In the case of using lithium hydroxybutyrate the level of consumption of alcohol reduced from 76.2 ml/kg to 58.5 ml/kg /$p<0.01$/. In terms of percent the diminution of pathological alcoholic motivation upon administration of lithium hydroxybutyrate was equal to 23.2% (in the case of lithium nicotinate it was 23.8%). In the case of lithium hydroxybutyrate even visually such phenomena as myorelaxation, considerable lowering of locomotive activity up to a complete adynamism, retardation were observed. In the case of lithium nicotinate these symptoms were absent which was indicative of the advantages of the preparation according to the present invention.

The thus-obtained data have found their reflection in the results of corresponding electrophysiological studies (Frequency-amplitude interrelationsip-electroencephalogram-EEG) which were analyzed after their histographic processing.

The study of the effect of chronic consumption of alcohol on the bioelectrical activity of cerebral cortex of white rats has shown that a lasting alcoholization causes decrease of amplitude and increase of frequency of EEG waves. On the 6-th and 12-th weeks of voluntary consumption of alcohol EEG prevail with a low-amplitude polymorphic activity, non-uniform (as regards frequency) $\alpha$-rhythms, clear-cut $\beta$-rhythms. Low bilateral paroxysms of a polymorphic character are frequently encountered. Similar data (desynchronization) but expressed to a greater extent were obtained in analysis of EEG of rats alcoholized during a 8-month's period and during abstinence.

The functional state of brains was also assessed by the reaction of the rhythm alteration in response to rhythmical light irritations of various frequencies. The study of the effect of chronic consumption of alcohol on the reaction of rhythm matching has shown that by the end of the 3-rd month of alcoholization, i.e. by the moment of formation of the "psychological" alcoholic dependence lowering of energy and reduction of the synchronization coefficient was observed. By the end of the 8th month of a voluntary consumption of ethanol and especially during the abstinence period the above-described variations of EEG were still more pronounced.

Administration of lithium nicotinate brings about unidirectional changes in the bioelectrical activity of brains. A slow-wave high-amplitude activity is being developed in the sight, sensomotor and audio areas of cortex of test animals. Administration of lithium nicotinate is accompanied by synchronization of all cortex potentials, increasing amplitude of all rhythms with a predominant increase of frequencies of $\Delta$ and $\theta$ ranges. It should be noted that under the influence of a course administration of lithium nicotinate not only unit waves appear but, what is most important, also group high-amplitude slow waves of the "spindle" type. Lithium chloride and lithium carbonate also caused synchronization of EEG upon their course administration. However, lithium nicotinate possessed a higher synchronizing effect as compared to lithium carbonate and lithium chloride.

The study of the effect produced by lithium nicotinate on the reaction of taking the rhythm in "alcoholic" rats has shown that it changes the ratio of processes of excitation and inhibition in the brain cortex: the range of assimilated frequencies is widened, the synchronization energy is increased. With nearly the same qualitative, but with a considerably smaller quantitative effect lithium chloride and lithium carbonate demonstrate their influence. In the case of using lithium nicotinate $K_s$ and $\Sigma A_s$ were certainly increased with application of relatively high (30 Hz) and relatively low (5 Hz) frequencies. In the animals treated with lithium chloride and lithium carbonate upon application of intermittent light of a low frequency the values of $K_2$ and $\Sigma A_s$ remained unchanged.

Tables 8, 9 and 10 show the effect of lithium nicotinate, lithium chloride and lithium carbonate respectively on the reaction of alteration of rhythm in rats alcoholized during the periods of 3, 8 and 10 months, as well as during the period of abstinence.

TABLE 8

| No. | | Testing period | Statistical parameters | Synchronization coefficient value (in percent) Applied frequency | |
|---|---|---|---|---|---|
| | | | | 5 Hz | 30 Hz |
| 1 | 1. | Initial data | M | 99.2 | 98.7 |
| 2 | | | ±m | 0.74 | 0.83 |
| 3 | 2. | 6 weeks of alcoholization | M | 97.9 | 95.4 |
| 4 | | | ±m | 1.55 | 2.08 |
| 5 | | | P 2–1 | >0.05 | >0.05 |
| 6 | 3. | 12 weeks of alcoholization | M | 87.9 | 82.6 |
| 7 | | | ±m | 3.76 | 3.48 |
| 8 | | | P 3–1 | 0.001 | 0.001 |
| 9 | 4. | 1 week of administration of the preparation | M | 98.4 | 94.7 |
| 10 | | | ±m | 0.99 | 2.48 |
| 11 | | | P 4–1 | >0.05 | >0.05 |
| 12 | | | P 4–3 | <0.05 | <0.01 |
| 13 | 5. | 2 weeks of administration of the preparation | M | 98.7 | 95.9 |
| 14 | | | ±m | 0.55 | 2.93 |
| 15 | | | P 5–1 | >0.05 | >0.05 |
| 16 | | | P 5–3 | <0.05 | <0.01 |
| 17 | 6. | 1 week after cancellation of the preparation | M | 96.6 | 94.2 |
| 18 | | | ±m | 2.4 | 2.29 |
| 19 | | | P 6–1 | >0.05 | >0.05 |
| 20 | | | P 6–3 | <0.1 | <0.1 |
| 21 | 7. | 5 months of alcoholization | M | 85.3 | 77.6 |
| 22 | | | ±m | 4.05 | 2.65 |
| 23 | | | P 7–1 | 0.001 | 0.001 |
| 24. | 8. | 8 months of alcoholization | M | 80.3 | 76.6 |
| 25 | | | ±m | 3.72 | 3.76 |
| 26 | | | P 8–1 | <0.001 | <0.001 |
| 27 | 9. | 1 week of administration of the preparation | M | 91.2 | 86.2 |
| 28 | | | ±m | 2.75 | 2.97 |
| 29 | | | P 9–1 | <0.02 | <0.01 |
| 30 | | | P 9–8 | <0.05 | <0.1 |
| 31 | 10. | 2 weeks of administration of the preparation | — | 95.8 | 94.5 |
| 32 | | | ±m | 2.48 | 1.95 |
| 33 | | | P 10–1 | >0.05 | 0.1 |
| 34 | | | P 10–8 | <0.01 | <0.001 |
| 35 | 11. | One week after cancellation | M | 94.1 | 93.5 |
| 36 | | | ±m | 2.16 | 1.92 |
| 37 | | | P 11–1 | <0.05 | <0.05 |
| 38 | | | P 11–8 | <0.01 | <0.001 |
| 39 | 12. | 10 months of alcoholization | M | 73.0 | 72.6 |
| 40 | | | ±m | 3.96 | 4.09 |
| 41 | | | P 12–1 | <0.001 | <0.001 |
| 42 | 13. | Period of abstinence | M | 71.3 | 70.0 |
| 43 | | | ±m | 3.85 | 2.44 |
| 44 | | | P 13–1 | <0.001 | <0.001 |
| 45 | 14. | One week of administration of the preparation against the background of abstinence | M | 94.4 | 96.6 |
| 46 | | | ±m | 3.18 | 1.19 |
| 47 | | | P 14–1 | >0.05 | >0.05 |
| 48 | | | P 14–12 | <0.001 | <0.001 |
| 49 | | | P 14–13 | <0.001 | <0.001 |

| No. | | Synchronization energy (in $\mu$V) Applied frequency | |
|---|---|---|---|
| | | 5 Hz | 30 Hz |
| 1 | 1. | 7,268.5 | 40,023.1 |
| 2 | | 887.6 | 6,169.1 |
| 3 | 2, | 5,053.1 | 31,714.3 |
| 4 | | 388.1 | 1,915.80 |
| 5 | | <0.05 | >0.05 |
| 6 | 3. | 4,733.3 | 23,943.3 |
| 7 | | 422.3 | 2,635.50 |
| 8 | | <0.02 | <0.02 |
| 9 | 4. | 6,053.0 | 39,287.0 |
| 10 | | 405.9 | 933.05 |
| 11 | | >0.05 | >0.05 |
| 12 | | <0.05 | <0.001 |
| 13 | 5. | 6,960.0 | 40,159.5 |
| 14 | | 652.30 | 4,738.37 |
| 15 | | >0.05 | >0.05 |
| 16 | | <0.01 | <0.01 |
| 17 | 6. | 6,560.0 | 35,059.5 |
| 18 | | 799.3 | 4,256.11 |
| 19 | | >0.05 | >0.05 |
| 20 | | <0.1 | <0.05 |

TABLE 8-continued

| | | | |
|---|---|---|---|
| 21 | 7. | 3,808.3 | 23,061.7 |
| 22 | | 262.27 | 2,307.56 |
| 23 | | <0.01 | <0.02 |
| 24 | 8. | 3,272.7 | 21,110.0 |
| 25 | | 374.51 | 1,622.0 |
| 26 | | <0.001 | <0.01 |
| 27 | 9. | 5,997.0 | 33,.686.0 |
| 28 | | 288.49 | 2,011.07 |
| 29 | | >0.05 | >0.05 |
| 30 | | <0.001 | <0.001 |
| 31 | 10. | 7,286.0 | 42,116.0 |
| 32 | | 515.26 | 2,478.28 |
| 33 | | >0.05 | >0.01 |
| 34 | | <0.001 | <0.001 |
| 35 | 11. | 6,478.0 | 33,952.0 |
| 36 | | 542.10 | 4,043.56 |
| 37 | | >0.05 | >0.05 |
| 38 | | <0.001 | <0.01 |
| 39 | 12. | 3,263.8 | 20,950.0 |
| 40 | | 500.92 | 1,757.94 |
| 41 | | >0.001 | <0.01 |
| 42 | 13. | 2,977.5 | 21,812.5 |
| 43 | | 379.11 | 2,110.13 |
| 44 | | <0.001 | <0.02 |
| 45 | 14. | 7,22.2 | 52,827.8 |
| 46 | | 508.74 | 875.96 |
| 47 | | | <0.1 |
| 48 | | <0.001 | <0.001 |
| 49 | | <0.001 | <0.001 |

TABLE 9

| No. | Testing period | | Statistical parameters | Synchronization coefficient, % Applied frequency | |
|---|---|---|---|---|---|
| 1 | 2 | | 3 | 5 Hz 4 | 30 Hz 5 |
| 1 | 1. | Initial data | M | 99.2 | 98.7 |
| 2 | | | ±m | 0.74 | 0.83 |
| 3 | 2. | 6 weeks of alco- | M | 97.9 | 95.4 |
| 4 | | holization | ±m | 1.55 | 2.08 |
| 5 | | | P 2-1 | >0.05 | >0.05 |
| 6 | 3. | 12 weeks of al- | M | 87.9 | 82.6 |
| 7 | | coholization | ±m | 3.76 | 3.48 |
| 8 | | | P 3-1 | <0.001 | <0.001 |
| 9 | 4. | One week of ad- | M | 89.8 | 89.8 |
| 10 | | ministration of | ±m | 3.91 | 3.04 |
| 11 | | the preparation | P 4-1 | <0.05 | <0.02 |
| 12 | | | P 4-3 | >0.05 | >0.05 |
| 13 | 5. | 2 weeks of ad- | M | 90.1 | 93.3 |
| 14 | | ministration | ±m | 4.00 | 3.97 |
| 15 | | of the prepara- | P 5-1 | 0.05 | >0.05 |
| 16 | | tion | P 5-3 | >0.05 | <0.05 |
| 17 | 6. | One week after cancel- | M | 88.6 | 91.4 |
| 18 | | lation of the prepa- | ±m | 4.90 | 1.43 |
| 19 | | ration | P 6-1 | <0.05 | <0.01 |
| 20 | | | P 6-3 | >0.05 | <0.05 |
| 21 | 7. | 5 months of alcoho- | M | 85.3 | 77.6 |
| 22 | | lization | ±M | 4.05 | 2.65 |
| 23 | | | P 7-1 | <0.001 | <0.001 |
| 24 | 8. | 8 months of alcoho- | M | 80.3 | 76.6 |
| 25 | | lization | ±m | 3.72 | 3.76 |
| 26 | | | P 8-1 | <0.001 | <0.001 |
| 27 | 9. | 1 week of administ- | M | 77.1 | 86.9 |
| 28 | | ration of the pre- | ±m | 3.41 | 2.51 |
| 29 | | paration | P 9-1 | <0.001 | <0.001 |
| 30 | | | P 9-8 | >0.05 | <0.05 |
| 31 | 10. | 2 weeks of admini- | M | 76.8 | 87.8 |
| 32 | | stration of the preparation | ±m | 3.34 | 2.50 |
| 33 | 10. | 2 weeks of administ- | P 10-1 | <0.001 | <0.001 |
| 34 | | ration of the pre- paration | P 10-8 | >0.05 | <0.05 |
| 35 | 11. | One week after can- | M | 78.1 | 81.6 |
| 36 | | cellation of the pre- | ±m | 4.18 | 2.96 |
| 37 | | paration | P 11-1 | <0.001 | <0.001 |
| 38 | | | P 11-8 | >0.05 | >0.05 |
| 39. | 12. | 10 months of al- | M | 73.0 | 72.6 |
| 40 | | coholization | ±m | 3.96 | 4.09 |

TABLE 9-continued

| | | | | |
|---|---|---|---|---|
| 41 | | | P 12-1 | <0.001 | <0.001 |
| 42 | 13. | Period of absti- | M | 71.3 | 70.0 |
| 43 | | nence | ±m | 3.85 | 2.44 |
| 44 | | | P 13-1 | <0.001 | <0.001 |
| 45 | 14. | One-week admi- | M | 74.0 | 88.0 |
| 46 | | nistration of the | ±m | 2.58 | 3.48 |
| 47 | | preparation aga- | P 14-1 | <0.001 | <0.01 |
| 48 | | inst the backgro- | P 14-12 | >0.05 | <0.02 |
| 49 | | und of abstinence | P 14-13 | >0.05 | <0.001 |

| | | | | Synchronization energy value, μV Applied frequency | |
|---|---|---|---|---|---|
| | | | | 5 Hz | 30 Hz |
| No. | 1 | | | 6 | 7 |
| 1 | 1. | | | 7,268.5 | 40,023.1 |
| 2 | | | | 887.6 | 6,169.1 |
| 3 | 2. | | | 5,053.1 | 31,714.3 |
| 4 | | | | 388.1 | 1,915.8 |
| 5 | | | | <0.05 | >0.05 |
| 6 | 3. | | | 4,733.3 | 23,943.3 |
| 7 | | | | 422.3 | 2,635.5 |
| 8 | | | | <0.02 | <0.02 |
| 9 | 4. | | | 4,789.0 | 34,454.5 |
| 10 | | | | 303.8 | 3,451.34 |
| 11 | | | | <0.02 | >0.05 |
| 12 | | | | >0.05 | <0.05 |
| 13 | 5. | | | 4,905.0 | 37,173.5 |
| 14 | | | | 468.38 | 3,120.95 |
| 15 | | | | 0.05 | |
| 16 | | | | >0.05 | |
| 17 | 6. | | | 4,816.0 | 27,322.0 |
| 18 | | | | 549.18 | 2,077.23 |
| 19 | | | | <0.05 | <0.05 |
| 20 | | | | >0.05 | >0.05 |
| 21 | 7. | | | 3,808.3 | 23,061.7 |
| 22 | | | | 262.27 | 2,307.56 |
| 23 | | | | <0.01 | <0.02 |
| 24 | 8. | | | 3,272.7 | 21,110.0 |
| 25 | | | | 374.51 | 1,622.0 |
| 26 | | | | <0.001 | <0.01 |
| 27 | 9. | | | 3,721.0 | 31,681.7 |
| 28 | | | | 331.32 | 2,394.30 |
| 29 | | | | <0.001 | >0.05 |
| 30 | | | | >0.05 | >0.05 |
| 31 | 10. | | | 3,565.0 | 33,612.0 |
| 32 | | | | 331.32 | 3,197.77 |
| 33 | 10. | | | <0.001 | >0.05 |
| 34 | | | | >0.05 | >0.05 |
| 35 | 11. | | | 332.40 | 25,642.0 |
| 36 | | | | 308.69 | 1,915.94 |
| 37 | | | | <0.001 | <0.05 |
| 38 | | | | >0.05 | <0.1 |
| 39 | 12. | | | 3,363.8 | 20,950.0 |
| 40 | | | | 500.92 | 1,757.94 |
| 41 | | | | <0.001 | <0.01 |
| 42 | 13. | | | 2,977.5 | 21,812.5 |
| 43 | | | | 379.11 | 2,110.13 |
| 44 | | | | <0.001 | <0.02 |
| 45 | 14. | | | 4,744.4 | 45,905.6 |
| 46 | | | | 448.10 | 4,095.70 |
| 47 | | | | <0.02 | >0.05 |
| 48 | | | | <0.05 | <0.001 |
| 49 | | | | <0.01 | <0.001 |

TABLE 10

| No. | Testing period | | Statistical parameters | Synchronization coefficient, % Applied frequency | |
|---|---|---|---|---|---|
| | 1 | 2 | 3 | 5 Hz 4 | 30 Hz 5 |
| 1 | 1. | Initial data | M | 99.2 | 98.7 |
| 2 | | | ±m | 0.74 | 0.83 |
| 3 | 2. | 6 weeks of alco- | M | 97.9 | 95.4 |
| 4 | | holization | ±m | 1.55 | 2.08 |
| 5 | | | P 3-1 | >0.05 | >0.05 |
| 6 | 3. | 12 weeks of alco- | M | 87.9 | 82.6 |
| 7 | | holization | ±m | 3.76 | 3.48 |
| 8 | | | P 3-1 | <0.001 | <0.001 |

TABLE 10-continued

| No. | | | | | |
|---|---|---|---|---|---|
| 9 | 4. | 1 week of administration of the preparation | M | 89.5 | 92.2 |
| 10 | | | ±m | 3.54 | 2.42 |
| 11 | | | P 4-1 | <0.02 | <0.02 |
| 12 | | | P 4-3 | >0.05 | >0.05 |
| 13 | 5. | 2 weeks of administration of the preparation | M | 90.3 | 92.4 |
| 14 | | | ±m | 4.05 | 2.84 |
| 15 | | | P 5-1 | <0.001 | <0.05 |
| 16 | | | P 5-3 | >0.05 | <0.05 |
| 17 | 6. | 1 week after cancellation | M | 89.0 | 91.9 |
| 18 | | | ±m | 3.79 | 3.38 |
| 19 | | | P 6-1 | <0.02 | <0.01 |
| 20 | | | P 6-3 | >0.05 | <0.01 |
| 21 | 7. | 5 months of alcoholization | M | 85.3 | 77.6 |
| 22 | | | ±M | 4.05 | 2.65 |
| 23 | | | P 7-1 | <0.001 | <0.001 |
| 24 | 8. | 8 months of alcoholization | M | 80.3 | 76.6 |
| 25 | | | ±m | 3.72 | 3.76 |
| 26 | | | P 8-1 | <0.001 | <0.001 |
| 27 | 9. | 1 week of administration of the preparation | M | 82.8 | 88.8 |
| 28 | | | ±m | 2.70 | 2.78 |
| 29 | | | P 9-1 | <0.001 | <0.01 |
| 30 | | | P 9-8 | >0.05 | <0.02 |
| 31 | 10. | 2 weeks of administration of preparation | M | 82.9 | 86.2 |
| 32 | | | ±m | 3.70 | 2.80 |
| 33 | | | P 10-1 | <0.001 | <0.001 |
| 34 | | | P 10-8 | >0.05 | <0.05 |
| 35 | 11. | 1 week after cancellation of the preparation | M | 77.8 | 79.0 |
| 36 | | | ±m | 3.98 | 3.67 |
| 37 | | | P 11-1 | <0.001 | <0.001 |
| 38 | | | P 11-8 | >0.05 | >0.05 |
| 39. | 12. | 10 months of alcoholization | M | 73.0 | 72.6 |
| 40 | | | ±m | 3.96 | 4.09 |
| 41 | | | P 12-1 | <0.001 | <0.001 |
| 42 | 13. | Period of abstinence | M | 71.3 | 70.0 |
| 43 | | | ±m | 3.85 | 2.44 |
| 44 | | | P 13-1 | <0.001 | <0.001 |
| 45 | 14. | One-week of administration of the preparation against the background of abstinence | M | 71.3 | 86.6 |
| 46 | | | ±m | 2.86 | 2.74 |
| 47 | | | P 14-1 | <0.001 | <0.001 |
| 48 | | | P 14-12 | | <0.02 |
| 49 | | | P 14-13 | | <0.001 |

| | | Synchronization energy value, $\mu V$ Applied frequency | |
|---|---|---|---|
| No. | 1 | 5 Hz 6 | 30 Hz 7 |
| 1 | 1. | 7,268.5 | 40,023.1 |
| 2 | | 887.6 | 6,169.1 |
| 3 | 2. | 5,053.1 | 31,714.3 |
| 4 | | 388.1 | 1,915.8 |
| 5 | | <0.05 | >0.05 |
| 6 | 3. | 4,733.3 | 23,943.3 |
| 7 | | 422.3 | 2,635.5 |
| 8 | | <0.02 | <0.02 |
| 9 | 4. | 4,587.0 | 33,906.5 |
| 10 | | 385.67 | 2,100.55 |
| 11 | | <0.02 | >0.05 |
| 12 | | >0.05 | <0.01 |
| 13 | 5. | 5,488.0 | 37,742.0 |
| 14 | | 324.28 | 2,315.10 |
| 15 | | <0.1 | >0.05 |
| 16 | | >0.05 | 0.001 |
| 17 | 6. | 4,925.5 | 34,542.0 |
| 18 | | 326.84 | 2,843.18 |
| 19 | | <0.05 | >0.05 |
| 20 | | >0.05 | 0.01 |
| 21 | 7. | 3,808.3 | 23,061.7 |
| 22 | | 262.27 | 2,307.56 |
| 23 | | <0.01 | <0.02 |
| 24 | 8. | 3,272.7 | 21,110.0 |
| 25 | | 374.51 | 1,622.0 |
| 26 | | <0.001 | <0.01 |
| 27 | 9. | 3,263.0 | 29,616.0 |
| 28 | | 385.86 | 2,717.03 |
| 29 | | <0.001 | >0.05 |
| 30 | | >0.05 | 0.02 |
| 31 | 10. | 3,339.0 | 36,644.0 |
| 32 | | 233.55 | 3,671.64 |
| 33 | | <0.001 | >0.05 |
| 34 | | >0.05 | <0.01 |
| 35 | 11. | 3,480.0 | 25,930.0 |
| 36 | | 324.06 | 1,946.07 |
| 37 | | <0.001 | <0.05 |
| 38 | | >0.05 | <0.1 |
| 39 | 12. | 3,363.8 | 20,950.0 |
| 40 | | 500.92 | 1,757.94 |
| 41 | | <0.001 | <0.01 |
| 42 | 13. | 2,977.5 | 21,812.5 |
| 43 | | 379.11 | 2,110.13 |
| 44 | | <0.001 | <0.02 |
| 45 | 14. | 4,310.0 | 42,505.0 |
| 46 | | 621.01 | 3,199.60 |
| 47 | | <0.02 | |
| 48 | | | <0.001 |
| 49 | | <0.01 | <0.001 |

According to modern conceptions, synchronization of an electroencephalogram, retardation of the background rhythmics appearance of "spindles" in combination with alteration of the range and optimum of the rhythm assimilation are the most characteristic manifestation of intensification of processes of retardation in the brains and elimination of the focus of the alcoholic dominant (Zakusov V.V. Pharmacology of Central Synapses. M., 1975, "Meditsina" Publishing House, p. 143).

The multi-purpose experiments carried out with the view to study antialcoholic properties of lithium nicotinate in combination with its advantages found in comparison with the prior art preparations—lithium chloride, lithium carbonate lithium hydroxybutyrate demonstrate that the compound according to the present invention can be widely employed as an active principle in a pharmaceutical composition.

Lithium nicotinate was administered to all patients following the same procedure using injections (by 1 ml of a 10% solution in an ampule) or pellets (containing 0.1 g in a pellet). The single doses were 0.1–0.2 g, daily doses—0.3–0.6 g. Some patients with insufficiently strong motives for the treatment (12 persons) with stage II of alcoholism and 21 persons with stage III of alcoholism or with a clear state of abstinent syndrome (5 persons) were injected with the preparation (1.0 ml of a 10% solution intramuscularly) for 45 days. Other patients were given lithium nicotinate in a tabletted form. The persons in the state of heavy drinking period were administered, during the first 8 days, with 0.2 g of lithium nicotinate three times a day, then with 0.1 g three times a day. The duration of the treatment course was 45 days.

In order to find out the potentiation effect of lithium nicotinate, the preparation in the pelletized form (by 0.1 g three times a day) was administered to 28 patients simultaneously subjected to a detoxification therapy (intravenous administration of 5.0–10.0 ml of a 25% solution of magnesia; 20.0–40.0 ml of a 40% solution of glucose; 5% of sodium ascorbate; intramuscular administration of 2.0–3.0 ml of vitamins $B_1$, $B_6$, $B_{12}$). The patients of this group suffered from alcoholism of stage III; in all of the patients psychopatholike changes of personality. Excitation prevailed in 3 persons, discontinuous drops of spirit—in 11 persons, asthenia—in 9 persons, apathism—in 4 persons. As a rule, these patients were brought for the treatment in the state of heavy drinking or of a short abstinence. The duration of the last remission was less than 4 months. The total duration of alcoholization in 19 persons was more than 19 years, in 5 persons—10–15 years, in 3 persons—9 years. All the patients were treated under stationary conditions: 12 persons—for 4 and more times, 6 persons—3 times, 9 persons—2 times.

In general, lithium nicotinate was administered to 129 male persons aged from 24 to 59 years. In 69 patients alcoholism of stage II was diagnosed, in 61 persons-alcoholism of stage III. A considerable number of persons under observation were subjected to the treatment of chronic alcoholism under stationary conditions. Out of them treated in hospitals under stationary conditions for 4 and more times were 18 persons, 3 times—34 persons, 2 times—31 persons, 1 time—38 persons. For the first time 8 persons were subjected to the treatment. In these patients, as a rule, remissions were of a short duration: in 13 persons—less than 1 year, in 34 persons—less than 9 months, in 41 persons—less than 6 months, in other (33 persons)—less than 4 months.

The majority of the observed patients for a long time were devoted to strong beverages. 69 persons—for more than 15 years, 36 persons—for 10–15 years, 13 persons 5–10 years, 11 persons—less than 5 years.

Changes in personality were observed in the examined patients which extended to the degree of acuity of premorbid personality features (68 persons) and psychopathization of personality (61 persons). In the first group of patients with aggravations of premorbid personality features several types of personality changes could be found (asthenic type—41 persons, explosive type—6 persons, various kinds of the schizoid type—21 persons). Psychopatho—like changes were characterized by excitability—7 persons, periodic depressive episodes with signs of anxiety of an asthenic background—41 persons, apathism and selective aspontaniety prevailed in 13 persons.

In this category of patients the predominant leading syndromes were: (a) various kinds of the asthenic syndrome—astheno-depressive—40 persons, asthenohypochondriac—12 persons, asthenic—17 persons; (b) anxious-depressive syndrome—22 persons; (c) anxious-paranoid syndrome—12 persons: (d) explovive —13 persons; (e) apathic—13 persons. A control group of patients of a similar age and nosologic origin was composed of 86 persons. The results of therapy with lithium nicotinate were compared to the results of the treatment with lithium hydroxybutyrate. Clinical characteristics of this group did not substantially differ from that of the group of patients administered with lithium nicotinate.

The duration of a previous abuse of alcohol in 41 persons was more than 15 years; in 27 persons—10–15 years; in 12 persons—6–10 years; less than 5 years—in 8 persons. Previously subjected to a stationary treatment for several times (4 times and more)—15 persons; 3 times—21 persons; 2 times 24 persons; 1 time—22 persons; for the first time brought to the treatment were 5 persons.

The duration of the last remission up to one year was in 9 persons, up to 8 months—in 19 persons, up to 6 months—in 24 persons, less than 4 months—in 29 persons.

In this group of patients prevailed the following persons:

1. With various kinds of asthenic syndrome (asthenodepressive—28 persons; astheno-hypochondriac—15 persons, asthenic—9 persons).
2. With anxious-depressive syndrome—13 persons.
3. With anxious-paranoid syndrome—6 persons.
4. With apathic syndrome—8 persons.

In this group of patients in 49 persons aggravation of premorbid personality features was observed. The most clearly pronounced symptoms corresponded to the following types: asthenic—21 persons; explosive—4 persons; to different kinds of schizoid type —24 persons. Psychopatho-like changes of personality were characterized by excitability in 7 persons; by periodic depressive episodes with signs of anxiety against the asthenic background—in 26 persons; in 8 persons apathism and aspontaneity prevailed.

Out of selected persons 49 patients suffered from alcoholism of stage II, 37 persons—alcoholism of III stage.

The treatment with lithium nicotinate and with lithium hydroxybutyrate was started from the first day of hospitalization.

As a rule, delivered to the stationary treatment were patients in the state of a short-time remission (66 persons out of the test group and 50 persons of the control group) or in the state of abstinence (2–3 days)—56 persons of the test group and 32 persons of the control group; 7 persons of the test group and 4 persons of the control group were delivered to the hospital in the state of a hard drinking period.

Furthermore, lithium nicotinate was employed for the ambulatory treatment under the conditions of an industrial enterprise. Treated were patients suffering from alcoholism of stage I (13 persons) and alcoholism of stage II (11 persons). The patients of this group were administered with lithium nicotinate in the dose of 0.1 g three times a day during 3 months. In the course of treatment normalization of emotional and vegetative disorders was noticed. During the treatment and the following 4 months no "failures" were observed.

In cases where the treatment was combined with a psychotherapeutic technique (21 persons) the preparation was first presented to the patients as an agent incompatible in the organism with alcohol which was proved by the formation of a subjective feeling of disgust to alcohol. Prior to being checked out of the hospital the patients were injected with a single dose of lithium nicotinate intravenously (3.0 ml with 15.0 ml of a 40% solution of glucose). The preparation was called "torpedo" and against the background of clearly manifested vegetative reactions a negative attitude to alcohol was installed. In 13 cases remissions were as long as 9 months, in 5 cases—6 months, in 3 cases—2 months. The shortest remission periods were observed in patients suffering from alcoholism of stage III.

The results of therapy with lithium nicotinate are presented in Tables 11, 12, 13.

In Table 11 generalized results of the treatment of patients with lithium nicotinate are given. In Table 12—the results for patients suffering from alcoholism of stage II. In Table 13—the data illustrating treatment of patients suffering from alcoholism in stage III.

TABLE 11

| No. | Syndrome | Total number of patients | Full disappearance of the symptoms | Improvement considerable stable | Improvement considerable unstable | Improvement insignificant stable | Improvement insignificant unstable | Absence of the effect | Deterioration | Ratio of successful and unsuccessful therapy |
| --- | --- | --- | --- | --- | --- | --- | --- | --- | --- | --- |
| 1 | 2 | 3 | 4 | 5 | 6 | 7 | 8 | 9 | 10 | 11 |
| 1 | Anxious-depressive | 22 | 19 | 1 | 1 | 1 | 0 | 0 | 0 | 20/2 |
| 2 | Explosive | 13 | 9 | 1 | 1 | 1 | 1 | 0 | 0 | 10/3 |
| 3 | Anxious-paranoid | 12 | 11 | 0 | 1 | 0 | 0 | 0 | 0 | 11/1 |
| 4 | Apathic | 13 | 7 | 2 | 1 | 2 | 1 | 0 | 0 | 9/4 |
| 5 | Astheno-depressive | 40 | 34 | 3 | 2 | 1 | 0 | 0 | 0 | 37/3 |
| 6 | Astheno-hypohondriac | 12 | 8 | 2 | 1 | 1 | 0 | 0 | 0 | 10/2 |
| 7 | Asthenic | 17 | 14 | 2 | 0 | 1 | 0 | 0 | 0 | 16/1 |
|  | TOTAL: abs. | 29 | 102 | 11 | 7 | 7 | 2 | 0 | 0 | 113/16 |
|  | % | 00 | 79 | 8.6 | 5.3 | 5.3 | 1,5 | 0 | 0 | 87,6/12.4 |

TABLE 12

| No. | Syndrome | Total number of patients | Full disappearance of the symptoms | Improvement considerable stable | Improvement considerable unstable | Improvement insignificant stable | Improvement insignificant unstable | Absence of the effect | Deterioration | Ratio of successful and unsuccessful therapy |
| --- | --- | --- | --- | --- | --- | --- | --- | --- | --- | --- |
| 1 | 2 | 3 | 4 | 5 | 6 | 7 | 8 | 9 | 10 |
| 1. | Anxious-depressive | 13 | 12 | 1 | 0 | 0 | 0 | 0 | 0 | 13/0 |
| 2. | Explosive | 6 | 5 | 0 | 1 | 0 | 0 | 0 | 0 | 5/1 |
| 3. | Anxious-paranoid | 9 | 9 | 0 | 0 | 0 | 0 | 0 | 0 | 9/0 |
| 4. | Astheno-hyponondric | 9 | 6 | 2 | 1 | 0 | 0 | 0 | 0 | 8/1 |
| 5. | Astheno-depressive | 29 | 27 | 2 | 0 | 0 | 0 | 0 | 0 | 29/0 |
| 6. | Asthenic | 2 | 2 | 0 | 0 | 0 | 0 | 0 | 0 | 2/0 |

TABLE 13

| No. | Syndrome | Total number of patients | Full disappearance of the symptoms | Improvement considerable stable | Improvement considerable unstable | Improvement insignificant stable | Improvement insignificant unstable | Absence of the effect | Deterioration | Ratio of successful and unsuccessful therapy |
| --- | --- | --- | --- | --- | --- | --- | --- | --- | --- | --- |
| 1 | 2 | 3 | 4 | 5 | 6 | 7 | 8 | 9 | 10 |
| 1. | Anxious-depressive | 9 | 7 | 0 | 1 | 1 | 0 | 0 | 0 | 7/2 |
| 1. | Anxious-depressive | 9 | 7 | 0 | 1 | 1 | 0 | 0 | 0 | 7/2 |
| 2. | Explosive | 7 | 4 | 1 | 1 | 1 | 0 | 0 | 0 | 5/2 |
| 3. | Anxious-paranoid | 3 | 2 | 0 | 1 | 0 | 1 | 0 | 0 | 2/1 |
| 4. | Astheno-depressive | 11 | 7 | 1 | 2 | 1 | 0 | 0 | 0 | 8/3 |
| 5. | Astheno-hypohondriac | 3 | 2 | 0 | 0 | 1 | 0 | 0 | 0 | 2/1 |
| 6. | Asthenic | 15 | 12 | 2 | 0 | 1 | 0 | 0 | 0 | 14/1 |
| 7. | Apathic | 13 | 7 | 2 | 1 | 2 | 1 | 0 | 0 | 9/4 |

The results of the studies shown in the above Tables 11, 12 and 13 point out that the events of a full disappearance of psychopathic symptoms and of a considerable stable improvement were noted in 88% of the patients, while in 12% the therapeutic effect was of an unstable character. It was possible to attain a full disappearance of psychopathological symptoms in 79% of cases. The best results were obtained in therapy of patients suffering from alcoholism of stage II with various kinds of a depressive syndrome.

In psychoparmaceutical tests it is assumed that the efficiency of therapy by means of certain psychotropic preparation is determined to a great extent by an influence on so-called "target-syndromes". In the treatment with lithium nicotinate emotional disorders were regarded as such symptomocomplex. It is seen from Table 11 that lithium nicotinate was most efficient in the treatment of patients with anxious-depressive and astheno-depressive syndromes.

In all cases the leading place in the structure of the syndrome was occupied by the proper-thymic component of the apparent syndrome: domination of disturbance of the spirit with its clear-cut lowering, psychomotoric retardation was noted, asthenic symptoms, fear and anxiety. Insomnia and loss of appetite were also noticed. Lithium nicotinate was especially effective in the case of these syndromes prevailing. The symptoms of fear, anxiety were diminished, the spirit was improved, as well as sleep and appetite. The effect of the pharmaceutical preparation according to the present invention on these emotional disturbances in the case of alcoholism makes it possible to state that lithium nicotinate has a normothymic scope of action.

In addition to this effect mild tranquilization and stress-protective effects of the preparation according to the present invention were also revealed. According to the data of clinical studies, administration of lithium nicotinate brings about diminution of the feeling of fear, anxiety, irritability, lacrimation, increased infatigation, weakness, retardation. The preparation improves psychic workability, does not disturb coordinate of movements and causes no myorelaxation.

Subject to the requirements of methodical guidelines regarding tests of novel psychotropic pharmaceutical compositions, we have carried out analysis of the dynamics of some psychopathological disorders during the treatment that has enabled an assessment of specific features of the psychotropic effect of lithium nicotinate. To this end, the severity of individual symptoms was recorded in points in 17 features-symptoms on standardized charts prior to the treatment and in the course thereof. Dynamics of the most clearly manifested psychopathological features in 129 patients suffering from alcoholism of stages II and III respectively that determined their state in general is represented in Tables 14 and 15 hereinbelow. A certain number of patients corresponds to each features, as well as the expression of the features in absolute terms (points) and in per cent relative to the initial level (during various periods of the treatment).

ration according to the present invention on certain psychopathological disorders, i.e. to find out at the account of which symptoms there occurs, in general, an improvement of the patients' health on the whole. Though this approach seems to be rather oversimplified, since it does not take into consideration the role of features in the structure of a particular syndrome, nevertheless it enables determination of the spectrum of the psychotropic activity of the preparation.

TABLE 14

| No. 1 | Symptoms 2 | Number of patients 3 | Intensity of symptoms in points and in percent | | | | | | | |
|---|---|---|---|---|---|---|---|---|---|---|
| | | | prior to the treatment 4 | 3-rd day 5 | 8-th day 6 | 15-nd day 7 | 22-th day 8 | 29-th day 9 | 36-th day 10 | 45-th day 11 | on completion of the treatment 12 |
| 1. | Low spirit | 65 | 2.2 | 1.4 | 0.9 | 0.3 | 0.1 | 0.1 | 0.1 | 0 | 0 |
| 2. | | | 100 | 63.6 | 40.9 | 13.6 | 4.5 | 5.5 | 4.5 | 0 | 0 |
| 3. | Asthenization | 56 | 1.5 | 1.3 | 0.9 | 0.3 | 0.3 | 0.3 | 0.2 | 0.2 | 0.2 |
| 4. | | | 100 | 86.7 | 60.0 | 20.0 | 20.0 | 20.0 | 13.3 | 13.3 | 13.3 |
| 5. | Anxiety | 29 | 1.4 | 1.2 | 0.8 | 0.3 | 0.1 | 0.1 | 0.1 | 0.1 | 0.1 |
| 6. | | | 100 | 85.7 | 47,1 | 21.4 | 7.1 | 7.1 | 7.1 | 8.1 | 7.1 |
| 7. | Emotional stress | 40 | 1.7 | 1.3 | 1.0 | 0.4 | 0.2 | 0.2 | 0.2 | 0.1 | 0.1 |
| 8. | | | 100 | 76.3 | 59.8 | 23.5 | 11.7 | 11.7 | 11.7 | 5.9 | 5.9 |
| 9. | Hypohondricity | 37 | 1.5 | 1.3 | 1.1 | 0.9 | 0.5 | 0.5 | 0.3 | 0.3 | 0.3 |
| 10. | | | 100 | 86.7 | 73.3 | 60.0 | 33.3 | 33.3 | 20.0 | 20.0 | 20.0 |
| 11. | Explosiveness | 9 | 1.5 | 1.3 | 1.3 | 0.9 | 0.8 | 0.7 | 0.7 | 0.7 | 0.7 |
| 12. | | | 100 | 86.7 | 86.7 | 60.0 | 53.3 | 46.7 | 46.7 | 46.7 | 46.7 |
| 13. | Apathism | 8 | 1.3 | 1.0 | 0.6 | 0.3 | 0.3 | 0.3 | 0.1 | 0.1 | 0.1 |
| 14. | | | 100 | 76.9 | 46.2 | 23.1 | 23.1 | 23. | 7.7 | 7.7 | 7.7 |
| 15. | Showing-off | 5 | 1.8 | 1.4 | 1.0 | 1.0 | 0.9 | 0.9 | 0.7 | 0.7 | 0.7 |
| 16. | | | 100 | 77.8 | 55.6 | 55.6 | 50.0 | 50.0 | 38.9 | 38.9 | 38.9 |
| 17. | Reticence | 7 | 1.4 | 1.2 | 1.0 | 0.6 | 0.4 | 0.4 | 0.2 | 0.2 | 0.2 |
| 18. | | | 100 | 85.7 | 71.4 | 42.9 | 28.6 | 28.6 | 14.3 | 14.3 | 14.3 |
| | Astheno-vegetative disorders | | | | | | | | | | |
| 19. | Insomnia | 62 | 1.6 | 1.4 | 1.0 | 0.3 | 0.3 | 0.1 | 0.1 | 0.1 | 0.1 |
| 20. | | | 100 | 87.5 | 62.5 | 18.7 | 18.7 | 6.2 | 6.2 | 6.2 | 6.2 |
| 21. | Perspiration | 59 | 1.5 | 1.1 | 0.5 | 0.1 | 0.1 | 0.1 | 0.1 | 0.1 | 0.1 |
| 22. | | | 100 | 73.3 | 33.3 | 6.6 | 6.6 | 6.6 | 6.6 | 6.6 | 6.6 |
| 23. | Palpitation | 61 | 1.9 | 1.5 | 0.9 | 0.3 | 0.3 | 0.1 | 0.1 | 0.1 | 0.1 |
| 24. | | | 100 | 78.9 | 47.4 | 15.8 | 15.8 | 5.3 | 5.3 | 5.3 | 5.3 |
| 25. | Tremor | 68 | 1.7 | 1.6 | 1.4 | 0.6 | 0.4 | 0.1 | 0.1 | 0.1 | 0.1 |
| 26. | | | 100 | 94.1 | 82.3 | 35.3 | 23.5 | 5.8 | 5.8 | 5.8 | 5.8 |

TABLE 15

| No. 1 | Symptoms 2 | Number of patients 3 | Intensity of the symptom in points and in % | | | | | | | |
|---|---|---|---|---|---|---|---|---|---|---|
| | | | Before treatment 4 | 3-rd day 5 | 8-th day 6 | 15-nd day 7 | 22-th day 8 | 29-th day 9 | 36-th day 10 | 45-th day 11 | On completion therapy 12 |
| 1. | Low spirit | 54 | 2.2 | 2.4 | 1.0 | 0.9 | 0.3 | 0.3 | 0.1 | 0.1 | 0.1 |
| 2. | | | 100 | 63.6 | 45.4 | 40.9 | 13.6 | 4.5 | 4.5 | 4.5 | 4.5 |
| 3. | Asthenization | 61 | 1.5 | 1.3 | 1.2 | 0.9 | 0.6 | 0.3 | 0.3 | 0.3 | 0.3 |
| 4. | | | 100 | 86.7 | 80.0 | 60.0 | 40.0 | 20.0 | 20.0 | 20.0 | 20.0 |
| 5. | Anxiety | 44 | 1.4 | 1.2 | 1.0 | 0.8 | 0.5 | 0.3 | 0.3 | 0.3 | 0.1 |
| 6. | | | 100 | 85.7 | 71.4 | 47.1 | 35.7 | 21.4 | 21.4 | 21.4 | 7.1 |
| 7. | Emotional stress | 58 | 1.7 | 1.3 | 1.0 | 0.8 | 0.6 | 0.4 | 0.2 | 0.2 | 0.2 |
| 8. | | | 100 | 76.3 | 58.8 | 47.0 | 35.3 | 23.5 | 11.7 | 11.7 | 11.7 |
| 9. | Hypohondricity | 19 | 1.5 | 1.3 | 1.1 | 0.9 | 0.5 | 0.5 | 0.5 | 0.5 | 0.5 |
| 10. | | | 100 | 86.7 | 73.3 | 60.0 | 43.3 | 33.3 | 33.3 | 33.3 | 33.3 |
| 11. | Explosiveness | 20 | 1.9 | 1.5 | 1.5 | 0.9 | 0.9 | 0.9 | 0.9 | 0.8 | 0.8 |
| 12. | | | 100 | 78.9 | 78.9 | 52.8 | 47.4 | 47.4 | 47.4 | 42.4 | 42.4 |
| 13. | Apathism | 23 | 1.5 | 1.3 | 1.1 | 0.9 | 0.5 | 0.3 | 0.3 | 0.3 | 0.3 |
| 14. | | | 100 | 86.7 | 73.3 | 60.0 | 33.3 | 20.0 | 20.0 | 20.0 | 20.0 |
| 15. | Showing-off | 12 | 1.8 | 1.4 | 1.0 | 1.0 | 0.9 | 0.8 | 0.8 | 0.8 | 0.8 |
| 16. | | | 100 | 77.8 | 56.6 | 56.6 | 50.0 | 50.0 | 44.4 | 44.4 | 44.4 |
| 17. | Reticence | 12 | 1.4 | 1.2 | 1.0 | 0.6 | 0.4 | 0.4 | 0.4 | 0.4 | 0.4 |
| 18. | | | 100 | 85.7 | 71.4 | 42.9 | 28.6 | 28.6 | 28.6 | 28.8 | 28.6 |
| | Astheno-vegetative disorders | | | | | | | | | | |
| 19. | Insomnia | 53 | 1.6 | 1.4 | 1.0 | 0.3 | 0.3 | 0.3 | 0.1 | 0.1 | 0.1 |
| 20. | | | 100 | 87.5 | 62.5 | 18.7 | 18.7 | 18.7 | 18.7 | 8.2 | 8.2 |
| 21. | Perspiration | 59 | 1.5 | 1.3 | 1.1 | 0.5 | 0.3 | 0.1 | 0.1 | 0.1 | 0.1 |
| 22. | | | 100 | 86.7 | 73.3 | 33.3 | 20.0 | 6.6 | 6.6 | 6.6 | 6.6 |
| 23. | Palpitation | 56 | 1.9 | 1.5 | 0.9 | 0.3 | 0.3 | 0.3 | 0.1 | 0.1 | 0.1 |
| 24. | | | 100 | 78.9 | 47.4 | 15.3 | 15.8 | 15.8 | 5.3 | 5.3 | 5.3 |
| 25. | Tremor | 61 | 1.7 | 1.6 | 1.4 | 1.0 | 0.9 | 0.6 | 0.4 | 0.3 | 0.3 |
| 26. | | | 100 | 94.1 | 82.3 | 58.8 | 52.9 | 35.3 | 23.6 | 17.7 | 17.7 |

Analysis of Tables 14 and 15 makes it possible to draw conclusions regarding the influence of the prepa- As it follows from Tables 14 and 15, lithium nicotinate provides the most effective influence at properly thymic disturbances, i.e. low spirit, without any substantial relationship with the stage of alcoholism. Lithium nicotinate produced a marked effect on depressive symptoms already since the first day in doses of 0.3 to 0.6 g a day. It should be noted that the features underwent a gradual and most pronounced reduction. Also brain vessels, on the development of a venous congestion. As a result of therapeutic effect of lithium nicotinate there took place normalization of the vascular tone, improvement of brain blood circulation, reduction of phenomena of venous congestion.

The effect of lithium nicotinate on addiction to alcohol is further illustrated by the data of Table 16 hereinbelow.

TABLE 16

| Characteristics of addiction | Number of patients | | | | | | | | |
|---|---|---|---|---|---|---|---|---|---|
| | Before treatment | 3-rd day | 8-th day | 15-th day | 22-th day | 29-th day | 36-th day | 45-th day | On completion of treatment |
| 1 | 2 | 3 | 4 | 5 | 6 | 7 | 8 | 9 | 10 |
| 1. Reduced | | 52 | | | | | | | |
| 2. Disappeared | | 77 | 129 | 122 | 129 | 129 | 127 | 129 | 129 |
| 3. Increased | 129 | 0 | 0 | 7 | 0 | 0 | 2 | 0 | 0 |
| 4. Type of addiction changed | | 0 | 0 | 0 | 0 | 0 | 0 | 0 | 0 | subjected to a considerable and rapid reduction were emotional stress, anxiety, asthenization. However, the rate and degree of reduction of these disorders were slightly lower than in the case of depressive ones and depended on the structure of the syndrome in which such phenomena were noticed. As regards hypochondriac disorders of apathism, explosiveness, reticence and showing-off it should be noted that the level of the residual psychopathological symptoms was more significant.

It should be also noted that normathymic and tranquilization effects of lithium nicotinate are exhibited as a rule during already the first 8 days of the treatment, mainly in patients suffering from alcoholism of stage II. Continuation of the treatment results in a gradual diminution of other symptoms. The maximum effect of the preparation was observed mainly in patients with stage II of alcoholism during 15 days of therapy; later on the pace of elimination of psychopathological symptoms decreased. In patients suffering from alcoholism of stage III the preparation showed maximum effect by the 30-th day of stay in stationary hospital conditions. Later on there took place a slower diminution of the degree of intensity of psychopathological symptoms. The most resistant to the therapy with the preparation according to the present invention in patients suffering from alcoholism in stages II and III turned to be explosiveness and showing-off.

Analysis of the effect of lithium nicotinate on asthenovegetative disorders has made it possible to find out the degree of influence of the preparation on individual symptoms. Lithium nicotinate proved to be most effective for the removal of insomnia, tachycardia and tremor. Lithium nicotinate produced a marked influence on astheno-vegetative behaviour since the first day of treatment in doses of 0.3–0.6 g a day. It should be noted that astheno-vegetative disturbances underwent a maximum pronounced reduction during the first 3–4 days of treatment, whereafter the therapeutic effect rose at a lesser rate. This points to a certain vegetotropic effect of the preparation apparently caused by its normothymic and tranquilizing effects. Lithium nicotinate proved to be most efficient in respect of patients with vascular cerebral disturbances displayed on an rheoencephalogram through deceleration of elevation of the anacrotic phase, by reduction or increase of the dicrotic wave, its shift towards the base or summit, rounding of the summit and appearance of the venous wave. The changes observed on the part of the rheographic curve point to an increased tone or atonia of Essential advantage is reduction of addiction to alcohol under the effect of the preparation since the 3-rd day of the treatment. The maximum effect is attained by the 8-th day. Episodic short-term (1–2 days) outbreaks of an increased addiction to alcohol should be noted under the influence of factors of the external origination in patients suffering from alcoholism in stage III.

The issue of duration of administration of lithium nicotinate to patients suffering from alcoholism is of a great interest. The carried out observations have shown that the most clearly pronounced effect of the preparation was revealed during the first 15 days of its administration. Later on its rate of therapeutic effect stabilized. Therefore, it is apparently possible to apply an intensive therapy with lithium nicotinate in the dose of 0.6 g a day for 15 days followed by shifting to a supporting treatment in doses of 0.3 g a day.

Hyperemia of the face and of the upper half of the body as well as parasthesia encountered in some cases in the treatment with lithium nicotinate can be used as a therapeutical factor in carrying-out an emotional-stressing psychotherapy of alcoholism.

Comparison of the data obtained in the treatment with lithium nicotinate with the data of control groups has demonstrated its higher efficiency in arresting of astheno-vegetative disorders. As compared to a conventional detoxification therapy a therapeutic effect on individual symptoms was observed by 1–2 days earlier and was more profound and stable. It is necessary, in the control group, to combine the carried out therapy with tranquilization agents and antidepressants at further stages of the treatment.

Therefore, the foregoing enables the following conclusions:

1. Clinical studies have shown that lithium nicotinate is a highly effective preparation for the treatment of alcoholism which is revealed in lowering and reduction of addiction to alcohol, normalization of individual psychopathological and personality characteristics. The preparation does not substantially exhibit any undersirable side and toxic effects.
2. While producing a clearly pronounced tranquilizing and normothymic effects, the preparation is especially active in arresting abstinence—softening and acceleration of reduction of astheno-vegetative disorders.
3. While producing a clearly pronounced stress-protective effect under conditions of an emotional overstresses and being efficient in various kinds of depressive disturbances, lithium nicotinate under laboratory conditions provides a stable negative attitude towards alcohol, while as an agent of emotional-stress therapy it also protracted the remission period, in addition to the negative relation to alcohol.

4. Lithium nicotinate exhibits a clearly pronounced trophic effect: it normalizes vascular tone, improves brain circulation, reduces phenomena of venous congestion simultaneously with a detoxifying effect which is apparently associated with activation of processes of oxidizing phosphorylation in the brain, improvement of provision thereof with microergs.

5. As a daily average dose in therapy of alcoholism 0.3–0.6 g of the preparation are advisable.

What is claimed is:

1. A pharmaceutical preparation for prophylaxis and treatment of alcoholism comprising from about 10 to about 40 weight per cent of an active principle which is a nicotinic acid lithium salt semihydrate of the formula:

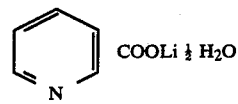

and a pharmaceutically acceptable vehicle.

2. A pharmaceutical preparation according to claim, 1 wherein said pharmaceutically acceptable vehicle is comprised of distilled water or an isotonic solution.

3. A pharmaceutical preparation according to claim 2 which is in the form of an injectable solution.

4. A pharmaceutical preparation according to claim 1, wherein said acceptable vehicle is comprised of at least one of stearic acid, lactose, glucose, potato starch and talc.

5. A pharmaceutical preparation according to claim 4 which is in the form of a pellets.

6. A method for treating a patient afflicted with alcoholism or under stress conditions which comprises administering to said patient a therapeutically effective amount of a pharmaceutical preparation of claim 1.

7. The method of claim 6 wherein said pharmaceutical composition is in the form of an injectable solution 8. The method of claim 6 wherein the pharmaceutical composition is in the form of a solid pellet.

* * * * *